United States Patent [19]

Teraoka et al.

[11] Patent Number: 4,780,530

[45] Date of Patent: Oct. 25, 1988

[54] NOVEL INTERFERON ALPHAS

[75] Inventors: Hiroshi Teraoka, Osaka; Kosaburo Sato, Hyogo; Kentaro Tanaka, Osaka, all of Japan

[73] Assignee: Shionogi & Co., Ltd., Osaka, Japan

[21] Appl. No.: 763,791

[22] Filed: Aug. 8, 1985

[30] Foreign Application Priority Data

Aug. 27, 1984 [JP] Japan .................................. 59-179105

[51] Int. Cl.$^4$ ..................... C07K 13/00; A61K 45/02; C12P 21/00
[52] U.S. Cl. .................................. 530/351; 424/85.7; 435/68; 435/811
[58] Field of Search .......................... 530/351; 424/85; 435/68, 172.3

[56] References Cited

PUBLICATIONS

Langer et al., J. Investigative Dermatology, vol. 33, pp. 1285–1365, 1984.

Primary Examiner—Blondel Hazel
Attorney, Agent, or Firm—Wenderoth, Lind & Ponack

[57] ABSTRACT

Novel IFNαS51B10 and IFNαS17H9 of this invention are prepared from BALL-1 cell induced with Sendai virus according to the well known recombinant DNA technique. Further, this invention relates to a DNA encoding interferon αS51B10 or αS17H9, a recombinant plasmid enabling an expression of interferon αS51B10 or αS17H9 in a host microorganism and a microorganism transformed by the recombinant plasmid. These two IFNαs have antiviral and anti-tumor activity as other subtypes of IFNα and are useful as medicines for human and animal.

1 Claim, 8 Drawing Sheets

```
        10        20        30        40        50        60
TGTGATCTGCCTCAGACTCACAGCCTGGGTAATAGGAGGGCCTTGATACTCCTGGCACAA
 C  D  L  P  Q  T  H  S  L  G  N  R  R  A  L  I  L  L  A  Q 70        80        90       100       110       120
ATGGGAAGAATCTCTCATTTCTCCTGCCTGAAGGACAGATATGATTTCGGATTCCCCCAG
 M  G  R  I  S  H  F  S  C  L  K  D  R  Y  D  F  G  F  P  Q 130       140       150       160       170       180
GAGGTGTTTGATGGCAACCAGTTCCAGAAGGCTCAAGCCATCTCTGCCTTCCATGAGATG
 E  V  F  D  G  N  Q  F  G  K  A  Q  A  I  S  A  F  H  E  M 190       200       210       220       230       240
ATCCAGCAGACCTTCAATCTCTTCAGCACAAAGGATTCATCTGCTGCTTGGGATGAGACC
 I  Q  Q  T  F  N  L  F  S  T  K  D  S  S  A  A  W  D  E  T 250       260       270       280       290       300
CTCCTAGACAAATTCTACATTGAACTTTTCCAGCAACTGAATGACCTAGAAGCCTGTGTG
 L  L  D  K  F  Y  I  E  L  F  Q  Q  L  N  D  L  E  A  C  V 310       320       330       340       350       360
ACACAGGAGGTTGGGGTGGAAGAGATTGCCCTGATGAATGAGGACTCCATCCTGGCTGTG
 T  Q  E  V  G  V  E  E  I  A  L  M  N  E  D  S  I  L  A  V 370       380       390       400       410       420
AGGAAATACTTTCAAAGAATCACTCTTTATCTGATGGGGAAGAAATACAGCCCTTGTGCC
 R  K  Y  F  Q  R  I  T  L  Y  L  M  G  K  K  Y  S  P  C  A 430       440       450       460       470       480
TGGGAGGTTGTCAGAGCAGAAATCATGAGATCCTTCTCTTTTTCAACAAACTTGCAAAAA
 W  E  V  V  R  A  E  I  M  R  S  F  S  F  S  T  N  L  Q  K 490       500
GGATTAAGAAGGAAGGATTGA
 G  L  R  R  K  D  *
```

```
         10        20        30        40        50        60
TGTGATCTGCCTCAGACCCACAGCCTGAGTAACAGGAGGACTTTGATGATAATGGCACAA
 C  D  L  P  Q  T  H  S  L  S  N  R  R  T  L  M  I  M  A  Q 70        80        90       100       110       120
ATGGGAAGAATCTCTCCTTTCTCCTGCCTGAAGGACAGACATGACTTTGGATTTCCTCAG
 M  G  R  I  S  P  F  S  C  L  K  D  R  H  D  F  G  F  P  Q 130       140       150       160       170       180
GAGGAGTTTGATGGCAACCAGTTCCAGAAGGCTCAAGCCATCTCTGTCCTCCATGAGATG
 E  E  F  D  G  N  Q  F  Q  K  A  Q  A  I  S  V  L  H  E  M 190       200       210       220       230       240
ATCCAGCAGACCTTCAATCTCTTCAGCACAAAGGACTCATCTGCTACTTGGGATGAGACA
 I  Q  Q  T  F  N  L  F  S  T  K  D  S  S  A  T  W  D  E  T 250       260       270       280       290       300
CTTCTAGACAAATTCTACACTGAACTTTACCAGCAGCTGAATGACCTGGAAGCCTGTATG
 L  L  D  K  F  Y  T  E  L  Y  Q  Q  L  N  D  L  E  A  C  M 310       320       330       340       350       360
ATGCAGGAGGTTGGAGTGGAAGACACTCCTCTGATGAATGTGGACTCTATCCTGACTGTG
 M  Q  E  V  G  V  E  D  T  P  L  M  N  V  D  S  I  L  T  V 370       380       390       400       410       420
AGAAAATACTTTCAAAGAATCACTCTCTATCTGACAGAGAAGAAATACAGCCCTTGTGCA
 R  K  Y  F  Q  R  I  T  L  Y  L  T  E  K  K  Y  S  P  C  A 430       440       450       460       470       480
TGGGAGGTTGTCAGAGCAGAAATCATGAGATCCTTCTCTTTATCAGCAAACTTGCAAGAA
 W  E  V  V  R  A  E  I  M  R  S  F  S  L  S  A  N  L  Q  E 490       500
AGATTAAGGAGGAAGGAATGA
 R  L  R  R  K  E  *
```

FIG. 3

```
         10        20        30        40        50        60
TGTGATCTGCCTCAGACTCACAGCCTGGGTAACAGGAGGGCCTTGATACTCCTGGCACAA
 C  D  L  P  Q  T  H  S  L  G  N  R  R  A  L  I  L  L  A  Q 70        80        90       100       110       120
ATGCGAAGAATCTCTCCTTTCTCCTGCCTGAAGGACAGACATGACTTTGAATTCCCCCAG
 M  R  R  I  S  P  F  S  C  L  K  D  R  H  D  F  E  F  P  Q 130       140       150       160       170       180
GAGGAGTTTGATGATAAACAGTTCCAGAAGGCTCAAGCCATCTCTGTCCTCCATGAGATG
 E  E  F  D  D  K  Q  F  Q  K  A  Q  A  I  S  V  L  H  E  M 190       200       210       220       230       240
ATCCAGCAGACCTTCAACCTCTTCAGCACAAAGGACTCATCTGCTGCTTTGGATGAGACC
 I  Q  Q  T  F  N  L  F  S  T  K  D  S  S  A  A  L  D  E  T 250       260       270       280       290       300
CTTCTAGATGAATTCTACATCGAACTTGACCAGCAGCTGAATGACCTGGAGTCCTGTGTG
 L  L  D  E  F  Y  I  E  L  D  Q  Q  L  N  D  L  E  S  C  V 310       320       330       340       350       360
ATGCAGGAAGTGGGGGTGATAGAGTCTCCCCTGATGTACGAGGACTCCATCCTGGCTGTG
 M  Q  E  V  G  V  I  E  S  P  L  M  Y  E  D  S  I  L  A  V 370       380       390       400       410       420
AGGAAATACTTCCAAAGAATCACTCTATATCTGACAGAGAAGAAATACAGCTCTTGTGCC
 R  K  Y  F  Q  R  I  T  L  Y  L  T  E  K  K  Y  S  S  C  A 430       440       450       460       470       480
TGGGAGGTTGTCAGAGCAGAAATCATGAGATCCTTCTCTTTATCAATCAACTTGCAAAAA
 W  E  V  V  R  A  E  I  M  R  S  F  S  L  S  I  N  L  Q  K

GATTGA
 D  *
```

■ TRP- PROMOTER OPERATOR AND SHINE- DALGARNO SEQUENCE
▨ SYNTHETIC OLIGONUCLEOTIDE ADAPTOR OR OLIGOMER
▨ IFNa cDNA-DERIVED DNA

■ TRP-PROMOTER OPERATOR AND SHINE DALGARNO SEQUENCE
▒ SYNTHETIC OLIGONUCLEOTIDE ADAPTOR OR OLIGOMER
▨ IFNa cDNA-derived DNA

NOVEL INTERFERON ALPHAS

BACKGROUND OF THE INVENTION (1) Field of the Invention

This invention relates to novel interferon alphas, namely interferon αS51B10 and interferon αS17H9. Further, it relates to DNA sequence and recombinant plasmid enabling an expression of these interferons and a microorganism transformed by the plasmid. The above interferon alphas each has antiviral and antitumor activity and is therefore utilized as a medicine for human and animal.

(2) Description of the Prior Art

Human interferon (hereinafter referred to as IFN) has α, β, and γ type, all of which are (glyco)proteins having antiviral activity and other broad physiological activities (W. E. Stewart II: The IFN System, Springer-Verlag, New York-Wien 1979).

It is well known that especially IFNα has many subtypes (S. Pestka: Arch. Biochem. Biophys 221, 1–37 (1983); C. Weissmann et al: Interferon, UCLA Symposia on Molecular and Cellular Biology 25, 295–326 (1982), Academic Press), and their antiviral, anti-cell proliferation and NK-activating activities are fairly different from each other's (E. Rehberg et al, J. Biol. Chem. 257, 11497 (1982)).

Leukocyte, Namalva cell, KG-1 cell and the like are recognized as producing a large amount of IFNα. From these cells mRNAs are extracted and the genes encoding sutypes of IFNα are isolated through cDNA cloning. However, the proportion of the amount of the subtypes containing is different in the each cell (I. Hiscott et al, Nucl. Acids. Res. 12, 3727–3746 (1984)).

Miyoshi et al found that BALL-1 cell isolated from leukemia leukocyte (I. Miyoshi et al, Nature 267, 843–844 (1977)) produces a lot of IFNα (Miyoshi et al, Progress in medicine (Igaku no ayumi) 113, 15–16 (1980)).

SUMMARY

Figure 2:
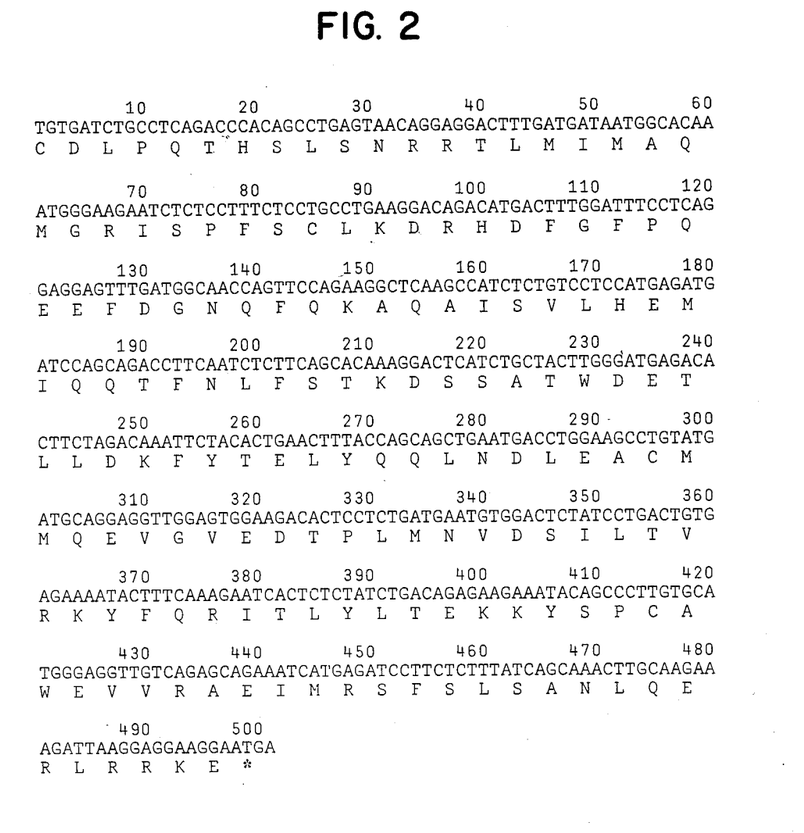
Figure 3:
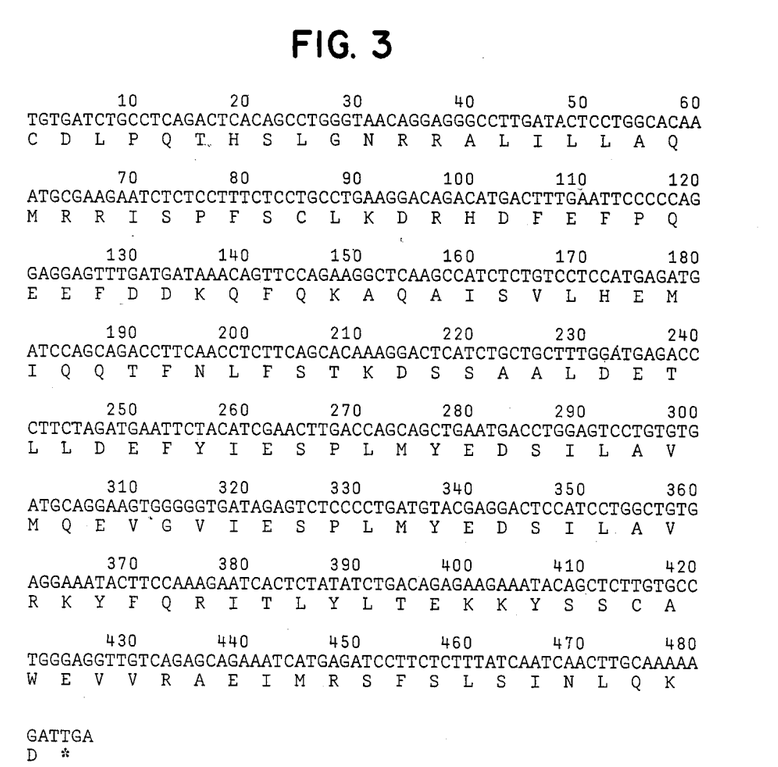

Novel IFNαS51B10 and IFNαS17H9 of this invention are prepared from BALL-1 cell induced with Sendai virus according to the well known recombinant DNA technique. Further, this invention relates to a DNA encoding interferon αS51B10 or αS17H9, a recombinant plasmid enabling an expression of interferon αS51B10 or αS17H9 in a host microorganism and a microorganism transformed by the recombinant plasmid. The IFNαS51B10 and IFNαS17H9 have DNA sequences, as shown in FIG. 2 and 3, respectively, different from those of all the already known subtypes of IFNα and so they are recognized as new. These two IFNαs have antiviral and anti-tumor activity as other subtypes of IFNα and are useful as medicines for human and animal.

DETAILED DESCRIPTION OF THE INVENTION

In order to discover novel IFN having potent IFN activity the inventors cultured BALL-1 cell and provided cDNA bank by well-known recombinant DNA technique, from which are isolated cDNAs of 2 types of IFNα different from every known type of IFNα. And the recombinant plasmids enabling the expression of the corresponding IFNαs were made by using these cDNAs. Then we transformed a microorganism with these plasmids and succeeded to produce the desired novel 2 types of IFNα.

Figure 1:
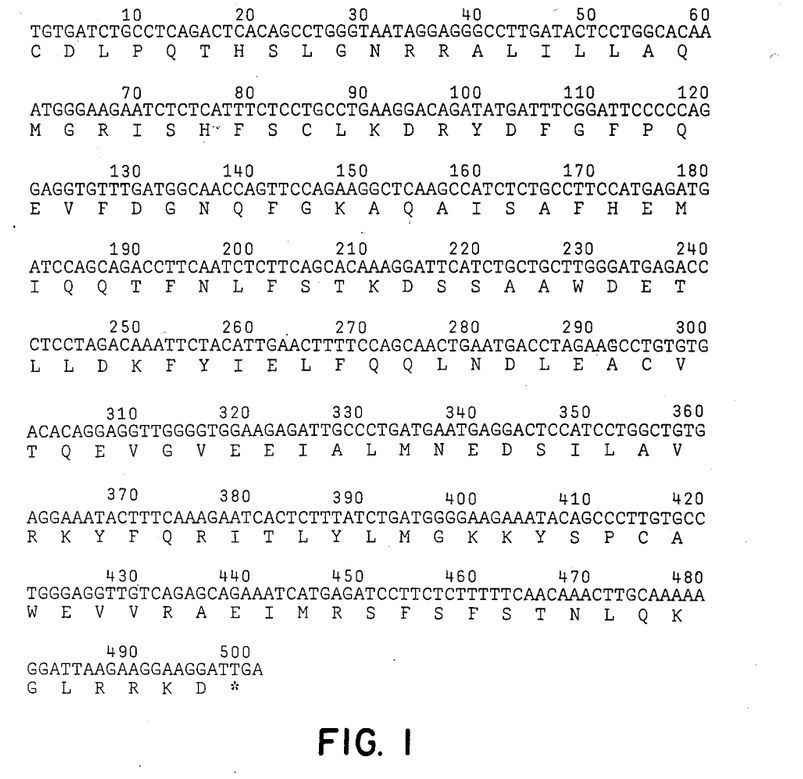
FIGS. 1–3 show the DNA sequence and the corresponding amino acid sequence of IFNαS80A2, IFNαS51B and IFNαS17H9, respectively.

A lot of complementary DNA (cDNA) clones were prepared by using as template IFNα mRNA separated from BALL-1 cell. Three clones were isolated from these clones, and one of them was already known one and other two clones were recognized as new from their base sequence and the amino acid sequence encoded thereby. The IFNs expressed by 3 clones were named IFNαS80A2, IFNαS51B10 and IFNαS17H9, respectively. The DNA sequences encoding these IFNs are shown in FIG. 1, FIG. 2 and FIG. 3 and the amino acid sequence of each IFNα deduced from the DNA sequence is shown under the DNA sequence in each Fig. Of course, every amino acid is of L type and represented in FIG. 1–3 by one letter defined by International Union of Biochemistry. What the letter means is as follows.

A: Alanine,
C: Cysteine,
D: Asparatic acid,
E: Glutamic acid,
F: Phenylalanine,
G: Glycine,
H: Histidine,
I: Isoleucine,
K: Lysine
L: Leucine,
M: Methionine,
N: Asparagine,
P: Proline,
Q: Glutamine,
R: Arginine,
T: Threonine,
V: Valine,
W: Tryptophan,
Y: Tyrosine.

Figure 4:
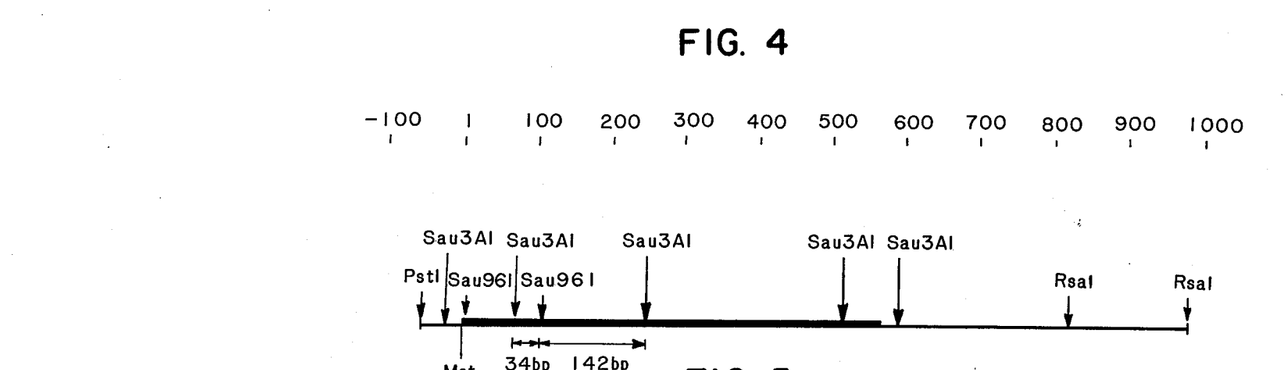
FIGS. 4–6 show the restriction map of cDNA of IFNαS80A2, IFNαS51B10 and IFNαS17H9, respectively, prepared from mRNA derived from BALL-1 cell.
Figure 5:
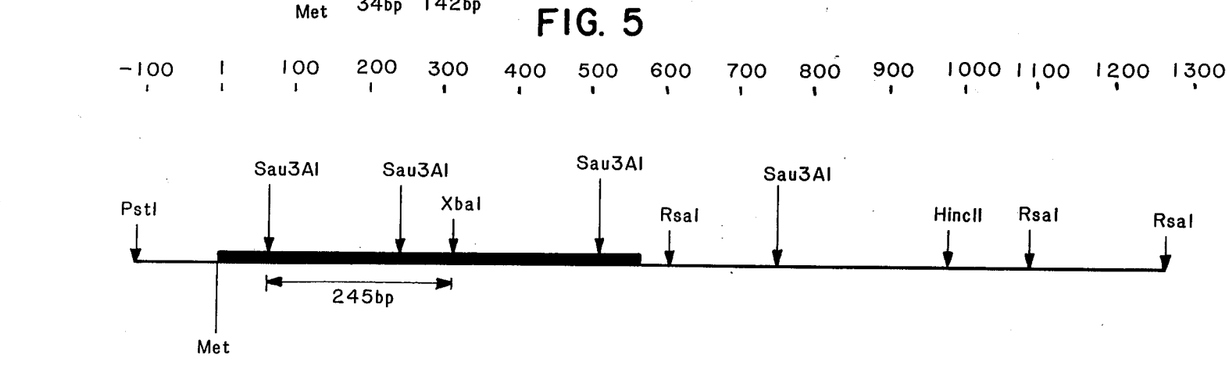
Figure 6:
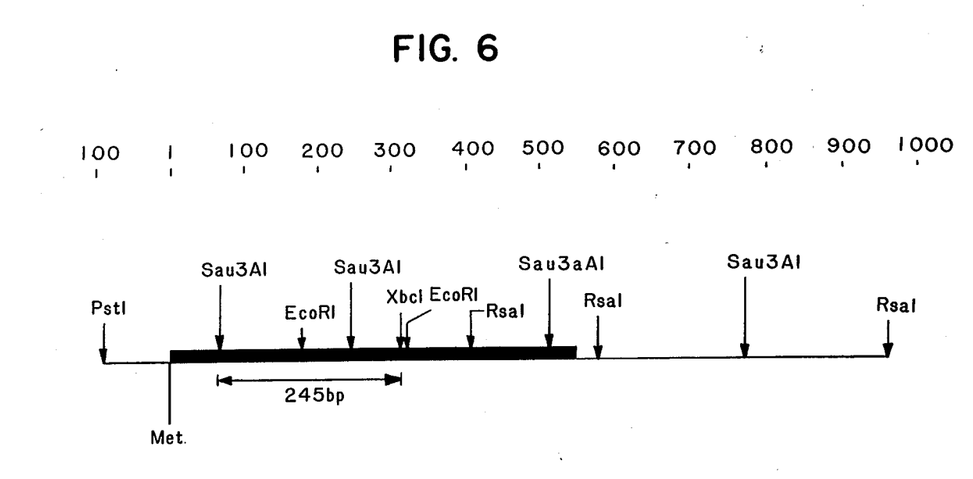

The restriction map by main restriction enzymes of each cDNA of IFNαS80A2, IFNαS51B10 and IFNαS17H9 derived from mRNA of BALL-1 cell is shown in FIG. 4, FIG. 5 and FIG. 6.

As shown in FIG. 1, the base sequence of IFNαS80A2 is the same as IFN-α-N reported by E. Gren et al (J. IFN Research 4, 609–617 (1984)).

IFNαS51B10 (FIG. 2) is very similar to IFNαG (Goeddel et al Nature 290, 20–26 (1981)) and IFNα5 (Weissman, the same as noted above). A part of the base sequence of αG has not yet been elucidated and the 33 amino acid residues from N terminal cannot be presumed. Therefore, it is impossible to determine if IFNαS51B10 is the same as αG. Since as to α5 the amino acid sequence only has been reported, compared with the amino acid sequence of αS51B10, the sole difference is recognized at 51th amino acid which is Lysine in α5 but Alanine in αS51B10. However, αS51B10 produced by *E. coli* shows antiviral activity in mouse cells but α5 produced by *E. coli* in the similar manner does not show antiviral activity in mouse cells (Nagata et al. Abstract of Japanese Virus Congress, 130, 1984; Proc. Natl. Acad. Sci. USA, 81, 5056–5090 (1984)). Thus, the chemical structure of subtype S51B10 of IFNα is similar to that of known α5, but a remarkable difference is recognized in physiological activity, and so IFNαS51B10 is determined to be novel IFNα.

IFNαS17H9 (FIG. 3) resembles known α8. Though all subtypes of IFNα consist of 166 amino acid residues except α2 (or αA) consisting of 165 amino acid residues (S. Pestka, the same as noted above, Weissmann, the same as noted above), this subtype consists of 161 amino acid residues. Therefore, it is recognized as novel IFNα.

By using cDNAs of IFNαs of this invention the recombinant plasmid expressing each IFNα is prepared according to well known recombinant DNA technique. The plasmid provided is introduced into an appropriate microorganism to give a transformed microorganism. Desired IFNα is produced by this microorganism. This invention comprehends IFNαS51B10 and IFNαS17H9 produced by this serial method, recombinant plasmids expressing them and microorganisms transformed with these plasmids.

Reagents, methods and operations used in the production of the desired materials as mentioned above are shown below. However, the present invention is not limited by these disclosures. In the following disclosures "IFNαs" is used as a general term of IFNαS80A2, IFNαS51B10 and IFNαS17H9.

I

PREPARATION OF cDNA i

Reagent and Method

A. Used Microorganism

A used microorganism is already known *Escherichia coli* K-12 such as HB101, χ1776, JM103, C600 and so on, *Bacillus subtilis* such as Maburg 168, *Saccharomyces cerevisiae* and the like. These microorganisms are available from authorized depositories such as American Type Culture Collection.

These microorganisms conform to Japanese guide line for recombinant DNA experimentation and this experiment was carried out according to the experimental guide line.

B. Used Enzymes, Reagents and Methods

Several kinds of restriction enzymes, DNA polymerase, T4 kinase, S1 nuclease, terminal deoxynucleotidyl transferase, reverse transcriptase, RNase H, DNA ligase and so on are all on the market. Human placenta RNase inhibitor is prepared in accordance with Blackburn's method (P. Blackburn, J. Biol. Chem. 254, 12484–12487 (1979)). Plasmid DNA and vector DNA on the market can be used. Recombinant plasmid of this invention is prepared by the standard alkali-SDS method (Birnboin et al, Nucl. Acids, Res. 7, 1513–1523 (1979)) and purified with CsCl. Sequencing of DNA is achieved by chain termination method of Sanger et al using M13 phage (F. Sanger et al, Proc. Natl. Acad. Sci, USA 74, 5463–5467 (1977)). Other general recombinant DNA techniques are detailed in and conform to Methods in Enzymology (Recombinant DNA), Vol. 68 (part A), Vol. 100 (part B) and Vol. 101 (Part C).

C. Chemical Synthesis of Oligodeoxynucleotide

Oligodeoxynucleotide can be synthesized by using dideoxynucleotide as consitution block (Broka et al, Nucleic Acids Res. 8, 5461–5471 (1980)) according to improved phosphotriester solid phase synthesis (Miyoshi et al, Nucleic Acids Res. 8, 5491–5505 (1980)). Material for the synthesis and the general method noted in Miyoshi et al, Nucleic Acids Res. 8, 5507–5517 (1980) are preferably used.

Oligonucleotide used as adaptor noted later is provided by linking specified dinucleotide or mononucleotide to 5' terminal. Mixed probe disclosed later is synthesized according to the method of Ike et al. (Nucleic Acids Res. 11, 477–488 (1983)).

ii

Operation

Usual genetic operation can be applied to the preparation of cDNA encoding IFNαs of this invention and the operation is shown below.

(a) Induction of IFNα in BALL-1 Cell

BALL-1 cell (human lymphoblastoid cell) is cultured in growth medium, primed as occasion demands and then induced with IFN-production inducer (for example, Sendai virus) so as to produce IFN.

(b) Preparation and Measurement of IFNmRNA

A change of the concentration of IFNmRNA produced in cultured cells of (a) with the passage of time is measured and when the concentration reaches to maximum the mRNA containing poly (A) is collected from the cultured cells by phenol extract and oligo (dT) cellulose chlomatography reported by Green et al. (Arch. Biochem. Biophys. 172, 74–89 (1975)).

(c) Synthesis and Cloning of cDNA

The cDNA can be prepared from mRNA according to the usual method and preferably be prepared by cloning according to Okayama-Berg's method (Med. Cell. Biol. 2, 161–170, (1982)) developed by Okayama and Berg.

(d) Preparation of Oligodeoxynucleotide probe

The $^{32}$P-oligodeoxynucleotide probe is prepared in order to search cDNA of IFNα from cDNA prepared in the above step. For example, the sequence complementary to the sequence of 62th to 77th from ATG of the DNA of each IFNα subtype is used as probe in accordance with the report of Goeddel et al. (Nature 290, 20–26 (1981)).

(e) Screening of cDNA by the Above Probe

The cDNA of IFNα is isolated by using the above probe. The isolation is preferably performed by colony hybridization (M. Grunsteins et al, Proc. Natl. Acad. Sci. USA 72, 3961–3965 (1975)).

(f) Analysis of IFNα cDNA

The clones having almost full-length IFNαcDNA are selected from the clones isolated in (e) and their restriction maps are made. The clones having restriction map different from that of already known IFNα are separated and their DNA sequences are determined to provide cDNAs of IFNαS51B10 and αS17H9. At the same time, the already known clone of IFNαS80A2 is separated and its DNA sequence is determined to prepare cDNA of IFNαS80A2.

The amino acid sequences of IFNαs of this invention are determined from cDNA sequences provided by the above procedure to give the results shown in FIGS. 1-3.

This invention comprehends every DNA encoding the amino acid sequence of IFNαS51B10 or αS17H9 and is not limited to the DNA shown in FIGS. 2-3.

II

PREPARATION OF EXPRESSION PLASMID i.

Reagents and Methods

Some conditions in this step is the same as exemplified in A, B, and C of the above I and other conditions are as follow.

D. Expression Vector

Several kinds of vectors of *E. coli* such as, for example, lac system, Trp system, Trp-lac fusion system, main operator and promoter system of λ-phage ($P_L$ etc.) and λ-phage reconstruction promoter ($CIP_RP_L$) (Tsurimoto et al, Mol. Gen. Genet. 187, 79–86 (1982)) are mainly employed. Yeast vector such as pFRPn(Hitzeman et al, Nature 293, 717–722 (1981)), Bacillus vector such as pKTH53 (Palva et al, Proc. of the IV International Symposium on Genetics of Industrial Microorganisms, (1982) 287-291) and so on can be employed, too.

E. Synthesized Oligodeoxynucleotide Adaptor

In order to express mature IFN in microorganisms it is necessary that the DNA sequence encoding signal peptide and upstream therefrom is removed from cDNA, initiation codon ATG is linked thereto and the resulting sequence is linked to promoter and introduced into microorganisms. Moreover, such the method is often used as oligodeoxynucleotide is inserted between Shine-Dalgarno (SD) sequence and ATG so that the expression amount of foreign protein is increased.

For example, in order to insert oligodeoxynucleotide causing the increase of the expression of IFNαs, in this invention the cDNA is cut by Sau3AI at between the codons encoding the first and the second amino acid of N-terminal of mature IFNαs. Therefore, such a synthesized oligomer is prepared as having a codon TGT encoding cysteine the first amino acid which is lost by the Sau3AI digestion and an initiation codon ATG and ClaI cutting site able to link to Trp-promoter (FIG. 7(*b*)). The examples are shown below.

(5') CGATACATGTGT
TATGTACACACTAG(5')

(5') CGATACTATATGTGT
TATGATATACACACTAG(5')

(5') CGATATATGTGT
TATATACACACTAG(5')

(5') CGATACTATGTGT
TATGATACACACTAG(5')

(5') CGATATTATGTGT
TATAATACACACTAG(5')

(5') CGATAGCTTTATGTGT
TATCGAAATACACACTAG(5')

F. Synthesized Deoxynucleotide Oligomer for ATG Vector

When an expression plasmid is prepared by using ATG vector, synthesized deoxynucleotide oligomer prescribing SD-ATG of appropriate kinds of bases and appropriate length is inserted into an expression vector. In this invention, since the synthesized deoxynucleotide oligomer is altered according to the properties of IFNαs, it is named Sn (n=integer of 7 to 20). The expression plasmid prepared by using ATG vector into which this oligomer pair is inserted is named pSn-IFNα. Therefore, ATG vector into which is inserted the following oligomer at one end of which has ClaI cutting site in order to employ Trp-promoter (FIG. 7(*b*)) and at another end of which has ATG and EcoRI cohesive and thereafter is provided to give the preferable result.

| | |
|---|---|
| (5') CGATACTATATG<br>TATGATATACTTAA (5') | (n = 11) |
| (5') CGATACATG<br>TATGTACTTAA (5') | (n = 8) |
| (5') CGATATATG<br>TATATACTTAA (5') | (n = 8) |
| (5') CGATACTATG<br>TATGATACTTAA (5') | (n = 9) |
| (5') CGATATTATG<br>TATAATACTTAA (5') | (n = 9) |

G. Method for the Preparation of Expression Plasmid

It is preferable to be referred to the method using a synthesized oligodeoxynucleotide adaptor (Goeddel et al, Nature 287, 411–416 (1980)) and the method by ATG vector (Nishi et al, DNA 2, 265–273 (1983)).

H. Insertion of Terminator

For the purpose of the increase of the production of IFN in *E. coli*, an already known terminator such as ribosomal RNA gene's terminator reported by Brosius et al (J. Mol. Biol. 148, 107–127 (1981), Gene 27, 161–172 (1984)) or phage gene's terminator reported by Krisch et al (Proc. Natl. Acad. Sci. USA 29, 4937–4941(1984)) is preferably inserted into the downstream of IFNαcDNA in the expression plasmid.

ii

Operation (g) Preparation of Expression Plasmid

The DNA sequence (FIGS. 1-3) encoding the amino acid sequence of mature IFNα is plasmid pIFNαs (FIGS. 4–6) provide by cloning in I is inserted into an expression vector having an appropriate promoter. The synthesized deoxynucleotide oligomer noted in E and F is used in this operation. This operation can be carried out according to already known method as noted in G. Moreover, as occasion demands a terminator is inserted.

The preparation of the expression plasmid for IFNαS80A2 using Trp-promoter is exemplified below.

(i) Example of Using Synthesized Oligonucleotide Adapter

1 The expression vector, pTrp-promoter vector (FIG. 7(*b*)) that promoter operator of Trp-operon and SD sequence of *E. coli* are inserted into plasmid pBR322 at ClaI cutting site is digested by ClaI and AccI to provide a fragment containing promoter. Plasmid pIFNαS80A2 (FIG. 7(*a*)) is digested by AccI and Sau96I to give a fragment having IFN structural gene, which is linked to the above fragment at AccI.

2 Plasmid pIFNαS80A2 is digested with Sau3AI to provide 176 bp fragment containing Sau96I site. This fragment is digested by Sau96I to give a mixture of 34 bp and 142 bp fragments having Sau3AI end and Sau96I end.

3 A synthetic oligodeoxynucleotide adaptor mentioned in E having initiation codon ATG and codon TGT encoding cysteine of N-terminal is synthesized.
4 The fragments and oligomer provided in above 1, 2 and (3) are linked to give plasmid pTrp-IFNαS80A2.

(ii) Example of Using ATG Vector

Figure 7A:
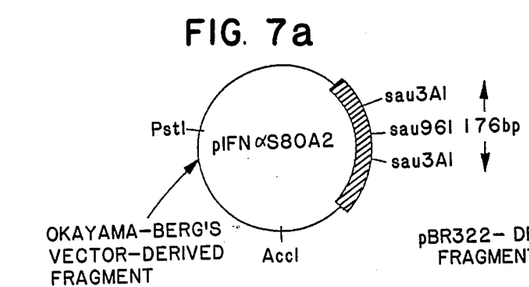
FIG. 7 shows the recombinant plasmid and the plasmid and vector used for the preparation thereof.
Figure 7B:
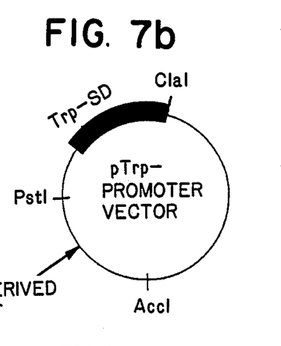
Figure 7C:
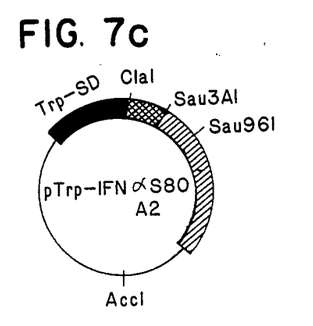
Figure 7D:
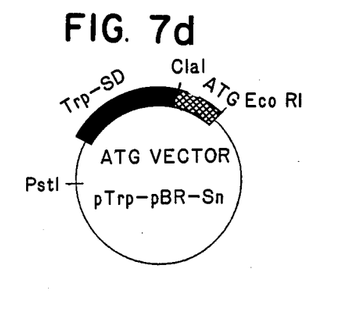
Figure 7E:
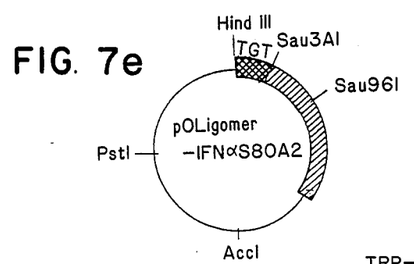
Figure 7F:
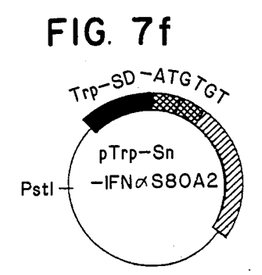
Figure 8:
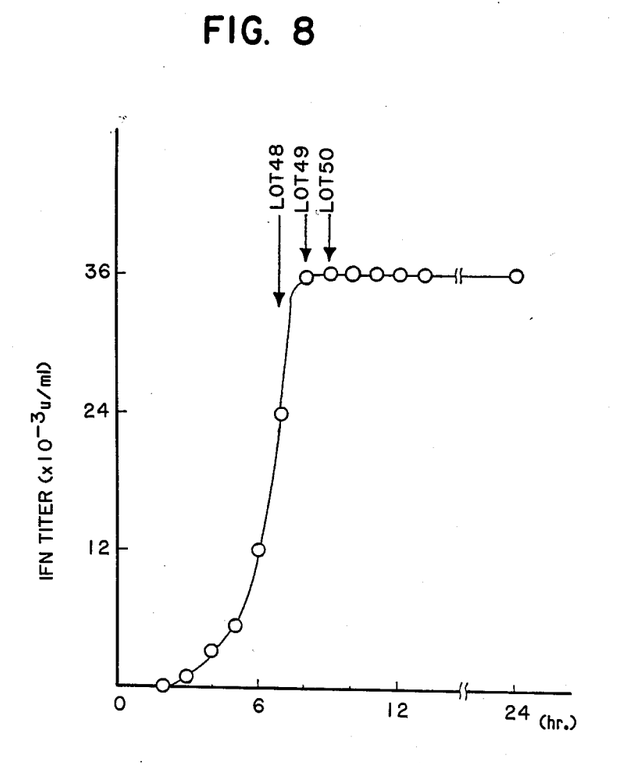
FIG. 8 shows the change of the production of IFN by BALL-1 cell with the passage of time.

1 Trp-promoter provided by digesting pTrp-promoter vector (FIG. 7(b)) with ClaI and PstI, pBR322 digester by PstI and EcoRI and a synthesized oligomer mentioned in above F are linked to provide ATG vector (FIG. 7(d)).
2 ATG vector is digested with EcoRI and S1 nuclease and then with PstI to give Trp-promoter fragment having PstI cohesive end, SD-ATG prescribed by Sn and ATG flush end.
3 Next, the plasmid from which the gene encoding signal peptide and the nucleotide sequence upstream therefrom in terms of a transcripting direction are removed and which carries IFN=cDNA is provided by employing synthesized deoxynucleotide oligomer ((5') CGAAGCTTGT and (5')GATCACAAGCTT). This oligomer complements the codon TGT which encodes cysteine of N-terminal amino acid of mature IFNα and which is lost by Sau3AI digestion, and introduces HindIII cutting site just before the codon (FIG. 7 (e), pOligomer IFNαS80A2).
4 The pOligomer IFNαS80A2 is digested with HindIII and S1 nuclease and then with PstII to give the fragment whose one end is flush end beginning with TGT and another end is PstI cohesive end that contains IFNαS80A2 structural gene.
5 The fragment of Trp-promoter (2) is linked to the fragment containing IFNαS80A2 structural gene (4) with T4 DNA ligase to provide pTrp-Sn-IFNαS80A2 (FIG. 7 (f)).

III

TRANSFORMATION AND EXPRESSION OF IFNα

According to the expression vector employed, the IFNα expression plasmid provided in II is introduced into an appropriate microorganism. In case using *E. coli* the transformation preferably achieved in accordance with the method of Hanahan et al, (J. Mol. Biol. 166, 557–580 (1983)). The resulting transformant is cultivated according to the usual method and the desired IFNα is separated from the culture and purified as occasion demands.

EXAMPLE

The present invention is exemplified by the following example but is never restricted by the example.

EXAMPLE 1

I.

Preparation of cDNA of IFNαS80A2

(a) Induction of IFNmRNA in BALL-1 Cell

Into growth medium RPMI 1640 medium containing 10% fetal calf serum) human lymphoblast cells are inoculated by $1-2 \times 10^5$ cells/ml and then incubated in $CO_2$ incubator at 37° C. for 3–4 days. After suspended to $8 \times 10^5$ cells/ml in growth medium containing 1 mM butyric acid, the cells are incubated at 37° C. for 48 hours and centrifuged by Sakuma 10B-2 rotor at 1200 rpm for 20 minutes. The resulting cells are suspended in growth medium (pH 7.2) containing 10 mM HEPES* to $5 \times 10^8$ cells/ml and treated with 100 IU/ml of IFNα with stirring at 100 rpm in a revolving incubating flask. After addition of 500–1000 hemagglutinin units/ml of Sendai virus (Cantell strain) the cells are incubated for 6–10 hours and collected by centrifugation by Sakuma 10B-2 rotor at 1200 rpm for 20 minutes.

*N-2-hydroxyethylpiperazine-N'-2-ethanesulphonic acid (b) Preparation and Measurement of IFNmRNA In order to collect cells when the amount of IFNmRNA therein reaches to maximum, a change of the production of IFN with the passage of time after the induction with Sendai virus is investigated (Table 8). After the induction with the virus, the cells incubated for 7, 8 or 9 hours are collected from each fraction to prepare mRNA. In order to estimate the rough amount of IFNmRNA in the obtained mRNAs, the mRNAs are injected into Xenopus oocyte according to the method of Cavalieri et al (Proc. Natl. Acad. Sci. 74, 3287 (1977)). After the oocytes are incubated at 20° C. for 48 hours, IFN activity in the medium is measured.

The IFN in the oocyte incubation medium is measured through cell Pathologically Effect (CPE) inhibition activity in MDBK cell challenged with vesicular stomatits virus. The result is shown in Table 1.

TABLE 1

| mRNA | IFN titer (u/μg mRNA) |
|---|---|
| Lot 48 (7 hr.) | 275 |
| Lot 49 (8 hr.) | 250 |
| Lot 50 (9 hr.) | 49 |

From the results of Table 1, it is recognized that the cells incubated for 7 hours after induced with the virus contain a lot of IFNmRNA. In order to condense the IFNmRA, mRNA prepared from the cells ($4 \times 10^9$ cells) at 7 hours after the induction with the virus is fractionated by 5–20% sucrose gradient centrifugation, a portion of each fraction is injected into Xenopus oocyte to investigate the IFN activity, and fractions around the 12S from which IFNmRNAs are always obtained is separated.

(c) Synthesis and Cloning of cDNA

The synthesis of the first strand cDNA by Okayama-Berg's method using 12S fraction mRNA is carried out in 50 μl of reaction mixture containing 1.5 μg of mRNA, 50 mM of Tris-HCl (pH 8.1), 50 mM of NaCl, 10 mM of $MgCl_2$, 10 mM of DTT, 0.2 mg/ml of bovine serum albumin (BSA), 220 u/ml of RNase inhibitor derived from human placenta, 5 μCi of ($\alpha$-$^{32}$P) dCTP and 2 mM of dATP, dCTP, dGTP and dTTP. As primer is used vector-primer provided by linking about 60 deoxythymidine residues to one end of DNA fragment constituting the vector, and 3.5 μg of vector primer (corresponding to 1.7 pmol) is used so that the number of mRNA molecule is in excess. After the addition of 50 u/ml of reverse transcriptase, the reaction mixture is incubated at 37° C. for 60 minutes. To the mixture 2 μl of 0.5M EDTA and 5 μg of poly (A) are added to stop the reaction, then the mixture is extracted with phenol-chloroform. To the extract the same part of 4M ammonium acetate (pH 5.0) and four parts of ethanol are added, and the mixture is cooled at −70° C. for 15 minutes and centrifuged for 10 minutes to give precipitate. The precipitate is dissolved in water again, and the procedure of the ethanol precipitation is carried out again. After washed with ethanol and lightly dried under reduced pressure, the precipitate is dissolved in water to advance to next step.

To the above precipitate (corresponding to 1.4 μg of vector-primer) is linked about 20 deoxycytidine residues at 3'-terminal using terminal deoxynucleotidyl transferase in 35 μl of reaction mixture containing 140 mM of sodium cacodylate, 30 mM of Tris-HCl (pH 6.8), 1 mM of CoCl₂, 0.1 mM of DTT, 0.1 mg/ml of BSA, 50 μCi of ($\alpha$-$^{32}$P) dCTP and 50 μM of dCTP. To the reaction mixture is added 16μ of terminal deoxynucleotidyl transferase, incubated at 37° C. for 15 minutes and cooled rapidly to 0° C. to interrupt the reaction, while, to measure the uptake of [$^{32}$P] into TCA precipitate, 1 μl of the mixture is sampled for estimating the length of deoxycytidine residues. If the length is about 20 bases, the reaction is stopped then, but if the linked chain is too short, the reaction mixture is warmed to 37° C. again to be allowed to react for appropriate time after the addition of the enzyme. The reaction is stopped by adding 2 μl of 0.5M EDTA, and the resultant is extracted with phenol-chloroform. To the extract are added one tenth parts of 3M sodium acetate (pH 5.3) and 2.5 parts of ethanol, and then ethanol precipitation and ethanol washing is carried out in the same manner as noted above. The precipitate is lightly dried under reduced pressure and recovered by dissolved in water.

The recovered precipitate is digested with HindIII in 20 μl of reaction mixture containing 10 mM of Tris-HCl (pH 7.5), 60 mM of NaCl, 7 mM of MgCl₂ and 0.1 mg/ml of BSA. To the reaction mixture 12μ of HindIII is added, and the mixture is incubated at 37° C. for 60 minutes and extracted with phenol-chloroform. The extract are precipitated by adding one tenth parts of 3M sodium acetate (pH 5.3) and 2.5 parts of ethanol thereto. The precipitate is lightly dried under reduced pressure and dissolved in water to obtain cDNA corresponding to about 0.8 μg of vector-primer.

The sample corresponding to 0.07 μg (0.035 pmol) of vector-primer is incubated with 13 ng (0.07 pmol) of linker DNA prepared by linking about 20 deoxyguanosine residues to one end of DNA fragment in 5 μl of 10 mM Tris-HCl (pH 7.5), 1 mM EDTA and 0.1M NaCl at 65° C. for 2 minutes, then at 42° C. for 30 minutes, and the mixture is cooled to 0° C. The following ingredients are added thereto to adjust the volume to 50 μl; 20 mM Tris-HCl (pH 7.5), 0.1M KCl, 4 mM MgCl₂, 10 mM (NH₄)₂SO₄, 0.1 mM β-NAD, 50 μg/ml BSA and 15 u of *E. coli* DNA ligase. Then the mixture is incubated overnight at 12° C.

The following ingredients are added to the reaction mixture so as to bring the specified concentration.: 40 mM of dATP, dCTP, dGTP and dTTP, 0.15 mM β-NAD, 10 u of *E. coli* DNA ligase (as additional part), 2.8 u of DNA polymelase I (Klenow Fragment) and 0.9 u of *E. coli* RNase H. The mixture is incubated at 12° C. for 1 hour and then at 25° C. for 1 hour.

By using this reaction mixture, *E. coli* K-12 (χ776 or HB101 strain) is transformed to form cDNA bank according to the method of Hanahan et al. (J. Mol. Biol. 166, 557-580 (1983)).

(d) Preparation of $^{32}$P-Oligodeoxynucleotide Probe

As a probe for screening human IFNα cDNA clone, two kinds of mixed probes consisting of 16 bases in chain length are prepared.

According to the Goeddel's report (Nature 290, 20-26, (1981)), these sequences are complementary to 62th to 77th sequence from ATG of each subtype cDNA of human IFNα. However, there is no base sequence whose length is more than 14 bases that is common in all subtypes. Therefore, we synthesize 2 types of 16-mer which are mixed type having 2 kinds of base at one site and are different at one site from one another in order to cover cDNAs of all IFNα subtypes.

The labeling of oligodeoxynucleotide with $^{32}$P is achieved by phospholylating with (γ-$^{32}$P)ATP and T4 polynucleotide kinase according to the method of Wallace et al (Nucl. Acids Res. 6, 3543-3557 (1979)). Moreover, (γ-$^{32}$P)ATP and T4 polynucleotide kinase which have not reacted is removed by gel filtration with Sephadex G-25.

(e) Screening of cDNA Clone with $^{32}$P-Synthesized Oligodeoxynucleotide

The clone containing human IFNα cDNA is detected from transformant resistant against ampicillin obtained by Okayama-Berg's method according to colony hybridization (M. Grunstein et al, Proc. Natl. Acad. Sci. USA 72, 3961-3965 (1975)).

On 125 sheets of nitrocellulose filter are formed 10,000 colonies, bacteriolysised with alkali and fixed after DNA denaturation. After pretreated with 4×SSC*, 10×Denhardt solution (Biochem. Biophys. Res. Comm. 23, 641-646 (1966)) and 100 μg/ml of *E. coli* DNA at 60° C. for 4 hours, the filters are hybridized at 35° C. for 15 hours with $^{32}$P-synthesized-oligodeoxynucleotide (chain length 16) probe (5×10⁵ cpm/filter) which is added to the newly prepared above-mentioned solution. After washed twice with 4×SSC at 4° C. for 15 minutes and air-dried, the filters are exposed at −70° C. to Kodak XAR-5 X-ray film by using Dupont lightening plus intensifying screen.

(*1×SSC contains 0.15M NaCl and 0.015M sodium citrate (pH 7.9))

(f) Analysis of cDNA of IFNα

Each plasmid DNA is prepared from 79 clones hybridized with synthetic oligonucleotide probe. Firstly, the plasmids are digested by PstI which cuts two sites of the vector to provide linear DNA, then 60 clones having insertion cDNA whose length is more than about 800 base pairs enough to contain human IFNα cDNA are selected.

Based on restriction enzyme map for each subtype of already known human IFNα, the subtype which each clone belongs to is presumed by making restriction maps for 60 clones according to the modified Southern hybridization, and then unknown clones and an already known clone (IFNαS80A2) are picked up.

Base sequence of cDNA clone (IFNαS51B10 and αS17H9) quite different from known ones is determined. Base sequence encoding each mature interferon and amino acid sequence deduced from the base sequence are shown in FIG. 1–FIG. 3. The main restriction map of each cDNA are shown in FIG. 4–FIG. 6.

II

Preparation of Expression Plasmid (g) Preparation of Expression Plasmid for IFNαS8-0A2

(i) Example of Using Synthesized Oligonucleotide Adaptor

1  Expression vector (pTrp-promoter vector) (FIG. 7(b)) that Trp-promoter-operator as promoter and SD sequence of E. coli are inserted into plasmid pBR322 at ClaI cutting site is used. This expression vector is digested with both ClaI and AccI and the fragment of ClaI-AccI which contains Trp-promoter is separated by polyacrylamide gel electrophoresis and cut out from the gel. The gel piece is broken in 10 mM Tris-HCl (pH8) and 1 mM EDTA and the supernatant is collected and precipitated with ethanol to recover DNA fragments. On the other hand, plasmid pIFNαS80A2 (FIG. 7(a)) is digested with both AccI and Sau96I and the fragment containing IFN structural gene is separated by the gel electrophoresis in the same manner. This fragment is linked to the above fragment carrying Trp-promoter with T4 ligase and the resulting fragment linked at AccI end is separated again by the gel electrophoresis.

2  Plasmid pIFNαS80A2 is digested by Sau3AI and 176 bp fragment having Sau96I site is separated by the gel electrophoresis (FIG. 7(a)). This fragment is digested by Sau96I to provide a mixture of 34 bp fragment and 142 bp fragment having Sau3AI end and Sau96I end.

3  Sau3AI cuts pIFNαS80A2 between the codon encoding the first amino acid and the codon encoding the second amino acid of N-terminal of mature IFN. Therefore, such synthesized oligodeoxynucleotide adaptor (5')CGATACATGTGT and (5') CATCACACATGTAT are prepared as has the codon TGT which encodes cysteine the first N-terminal amino acid and which is lost by Sau3AI digestion and the initiation triplet ATG for initiation of translation necessary in expression by E. coli.

4  The Trp-promoter-linked IFN structural gene fragment ( 1 ), the mixture of 34 bp fragment and 142 bp fragment ( 2 ) and the synthesized deoxynucleotide adaptor provided by annealing the two fragments ( 3 ) are linked with T4 ligase. With the resulting recombinant DNA is transformed E. coli K-12 according to the method of Hanahan et al.

The transformant is selected on a plate containing ampicillin. From the resulting colonies resistant against ampicillin are selected a few colonies, from which plasmid DNA is isolated. The presence of desired fragment is confirmed by the restriction enzyme analysis. The provided plasmid is named pTrp-IFNαS80A2 (FIG. 7(c)). Moreover, the extract of E. coli carrying this plasmid has antiviral activity as noted later.

(ii) Example of Using ATG Vector

1  The above pTrp-promoter vector (FIG. 7(b)) is digested by both ClaI and PstI and the fragment carrying Trp-promoter is isolated by the gel electrophoresis. Plasmid pBR322 is digested with both PstI and EcoRI and the longer fragment is isolated by the gel electrophoresis. These two fragments and annealed synthetic deoxynucleotide oligomer (Sn) consisting of (5')CGATACTATATG and (5')AATTCATATAGTAT (n=11) prescribing SD-ATG are linked with T4 ligase. E. coli K-12 is transformed with the resulting recombinant DNA according to the method of Hanahan et al (the same as noted above).

The transformant is selected on a plate containing ampicillin and a few colonies are selected therefrom. The completion of preparation of ATG vector is confirmed by the restriction enzyme analysis of plasmid DNA isolated from the selected colonies.

2  The above ATG vector is digested with EcoRI and then the EcoRI cohesive end is digested with S1 nuclease. After phenolchloroform extraction and ethanol precipitation, the resultant is digested by PstI and a fragment carrying Trp-promoter is separated by the gel electrophoresis. The fragment has PstI cohesive end, SD-ATG prescribed by Sn and flush end as a coding chain ends in ATG.

3  In the same manner as in (i), plasmid pIFNαS80A2 is digested with both AccI and Sau96I to give a fragment having IFNα structural gene. Plasmid pBR322 is digested with both ClaI and AccI and the longest fragment isolated by the gel electrophoresis is linked to the above DNA fragment at AccI cutting site with T4 ligase. In the same manner as in (i), Sau3AI fragment (176 bp) of plasmid pIFNαS80A2 is digested with Sau96I to give a mixture of 34 bp and 142 bp.

On the other side, such synthetic deoxynucleotide oligomers, (5')CGAAGCTTGT and (5')GATCACAAGCTT, are prepared as having the codon TGT at end which encodes the first amino acid (cysteine) of N-terminal of mature IFNα and which is lost by Sau3AI digestion and introducing HindIII cutting sit just before TGT.

The annealed above oligomers, the above pBR322-IFNα structural gene-linked fragment and the mixture of 34 bp and 142 bp are linked with T4 ligase. E. coli K-12 is transformed with the resulting recombinant DNA in the same manner as in (i). In the same way as in (i), plasmid DNA is separated and the completion of preparing the desired plasmid is confirmed through the restriction enzyme analysis. The resulting plasmid is named pOligomer-IFNαS80A2 (FIG. 7(e)).

4  The pOligomer-IFNαS80A2 prepared above is digested with HindIII and then the HindIII cohesive end is digested by S1 nuclease. After phenolchloroform extraction and ethanol precipitation, the resultant is digested by PstI and a fragment having IFNα structural gene is separated by the gel electrophoresis. The resulting fragment carrying IFNα structural gene has PstI cohesive end and flush end as a coding chain begins with TGT.

5  The fragment carrying Trp-promoter prepared in 2 is linked to the fragment carrying IFNα structural gene prepared in 4 and E. coli K-12 is transformed with the resulting recombinant DNA in the same manner as noted above.

Transformant is selected on a plate containing ampicillin. A few colonies are selected from the resulting colonies resistant against ampicillin and each clone is multiplied. The antiviral activity in the extract of the E. coli is measured in a manner noted later and the transformants having the antiviral activity are recovered. The base sequence of the plasmid held by these transformants is analyzed and the each linkage of promoter, SD-ATG and IFN structural gene is confirmed to be desired linkage. The plasmid recovered from these transformants is named pTrp-Sn-IFNαS80A2 (FIG. 7(f)) corresponding to the synthesized nucleotide oligomer Sn contained in ATG vector.

A standard strain of E. coli K-12 C600/pIFNαS80A2 prepared by transformation has been deposited as FERM P-7745 since July 25, 1984 in the Fermentation Research Institute Agency of the Industrial Science & Technology at Yatabe-machi, Tsukuba-gun, Ibaraki Pref. Japan.

EXAMPLE 2

(a) Preparation of Expression Plasmid for IFNαS17H9 and IFNαS51B10

From two kinds of cDNA clone (IFNαS17H9 and IFNαS51B10) prepared in the above example 1-I-f is prepared each expression plasmid in the same manner as in example 1. Since both IFN structural genes have similar restriction enzyme cutting sites to one another as shown in FIG. 5 and 6, procedures for preparing the expression plasmids are almost the same as one another. Therefore, a method for preparing both expression plasmids is shown below.

(i) Example of Using Synthesized Oligonucleotide Adaptor

By the method mentioned in example 1-(g)-(i) Trp-promoter vector (FIG. 7(b)) is digested with ClaI and PstI and a ClaI-PstI fragment having Trp-promoter is isolated.

On the other hand, plasmid pIFNαS17H9 or pIFNαS51B10 is digested with both PstI and XbaI and about 2.3 kbp fragment carrying the latter half of IFN structural gene is separated by the gel electrophoresis in the same way noted above. This fragment is linked to the previously separated fragment having Trp-promoter with T4 ligase and the fragment linked at PstI site is isolated again by the gel electrophoresis.

Figures 9A, 9B:
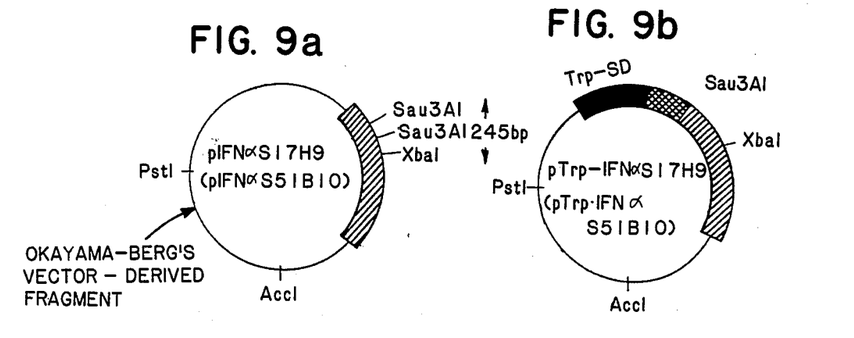
FIG. 9 shows the recombinant plasmid for the expression of IFNαS17H9 or IFNαS51B10 and the plasmid and vector used for the preparation thereof.

Then, plasmid pIFNαS17H9 or pIFNαS51B10 is digested with XbaI and next partially with Sau3AI and a 245 bp fragment having the former half of IFNα structural gene is isolated by the gel electrophoresis (see FIG. 9 (a)).

This 245 bp fragment, the above ClaI-XbaI fragment having Trp-promoter and annealed synthetic oligo-deoxynucleotide adaptor, (5')CGATACATGTGT and (5')GATCACACATGTAT, having initiation codon ATG and TGT encoding cysteine and amino acid of N-terminal of IFNα are mixed and linked with T4 ligase. With the resulting recombinant DNA is transformed E. coli K-12 according to the method of Hanahan et al.

The transformant is selected on a plate containing ampicillin. A few colonies are selected from the resulting colonies resistant against ampicillin, and plasmid DNA is isolated therefrom. The presence of the desired fragment is confirmed by the restriction enzyme analysis. The resulting plasmids are named pTrp-IFNαS17H9 and pTrp-IFNαS51B10, respectively (FIG. 9(c)). The extract of E. coli carrying this plasmid has antiviral activity as mentioned later.

(ii) Example of Using ATG vector

1  ATG vector (FIG. 7(d)) is prepared in the same manner as in example 1-(g)-(ii)- 1 and digested with EcoRI, S1 nuclease and PstI in the same way as in the same- 2 to give DNA fragment having PstI cohesive end, SD-ATG prescribed by Sn and flush end as coding chain ends in TAG.

2  PstI-XbaI fragment of plasmid pIFNαS17H9 or pIFNαS51B10 is prepared in the same manner as in (i). Plasmid pBR322 is digested with both ClaI and PstI and the shorter ClaI-PstI fragment is separated therefrom and linked to the above fragment at PstI site. On the other hand, Sau3AI-XbaI fragment consisting of 245 bp is prepared from plasmid pIFNαS17H9 or pIFNαS51B10 in the same manner as in (i).

3  On the other side, synthetic deoxynucleotide oligomers, (5')CGAAGCTTGT and (5')GATCACAAGCTT, which have the codon TGT at the end which encodes the first amino acid (cysteine) of N-terminal of mature IFNα and which is lost by Sau3AI digestion and introduce HindIII cutting site just before TGT, are prepared.

4  The above oligomer annealed, the fragment of pBR322-IFNα structural gene prepared in above 2 and 245 bp Sau3AI-XbaI fragment of IFNαS17H9 (or αS51B10) are linked with T4 ligase. With the resulting recombinant DNA is transformed E. coli K-12 in accordance with the method of Hanahan et al.

A plasmid is prepared from the transformant in the same way as in (i) and subjected to the restriction enzyme analysis to be confirmed that the desired plasmid is prepared.

Figure 9C:
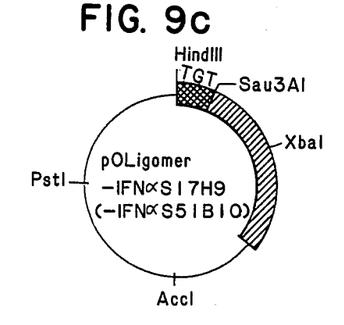

The plasmids provided are named pOligomer-IFNαS17H9 and pOligomer-IFNαS51B10, respectively (FIG. 9(c)).

5  The plasmid prepared in above 4 is digested with HindIII and the HindIII cohesive end is digested by S1 nuclease. After the phenol-chloroform extraction and the ethanol precipitation, the resultant is digested with PstI and the fragment carrying IFNα structural gene is separated by the gel electrophoresis. The fragment carrying IFNα structural gene has PstI cohesive end and flush end as a coding chain begins with TGT.

6  The fragment carrying Trp-promoter provided in above 1 is linked to the fragment carrying IFNα structural gene provided in above 5 with T4 ligase and with the resulting recombinant DNA is transformed E. coli K-12 (C600) in the same manner as noted above.

Figure 9D:
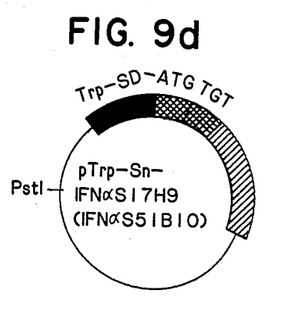

Transformant is selected on a plate containing ampicillin. A few colonies are selected from the resulting colonies resistant against ampicillin and each clone is amplified. The antiviral activity in the extract of the E. coli is measured in a manner noted later and the transformants having the antiviral activity are recovered. The base sequence of the plasmid held by transformants is analyzed and the each linkage of promoter, SD-ATG and IFN structural gene is confirmed to be a desired linkage. The plasmids recovered from these transformants are named pTrp-Sn-IFNαS17H9 and pTrp-Sn-IFNαS51B10, respectively (FIG. 9 (d)) corresponding to the synthesized nucleotide oligomer Sn contained in ATG vector.

The transformants provided in the above procedure are named Escherichia coli K-12 C600/pIFNαS17H9 and Escherichia coli K-12 C600/pIFNαS51B10, respectively, which have been deposited as FERM P-7766 and FERM P-7767, respectively, since Aug. 8, 1984 in the Fermentation Research Institute Agency of the Industrial Science & Technology and have been transferred to the deposition under the Budapest Treaty with accession No. FERM BP-840 and FERM BP-841, respectively, since July 11, 1985.

EFFECT OF THE INVENTION

I.

Expression of IFNαS80A2

(i) Analysis of the Production from Plasmid Gene by Using In Vitro Transcription-Translation System.

Zubay et al reported that protein encoded by plasmid DNA can be produced in in vitro transcription-translation system by using *E. coli* extract (Methods in Enzymology 65, 856–877 (1980)).

The recombinant plasmid pTrp-IFNαS80A2 having Trp-promoter provided above is allowed to react in the presence of $^{35}$S-methionine by using in vitro transcription-translation system kit (Amersham) according to the manual. The reaction production is analyzed by 16% SDS-polyacrylamide gel electrophoresis (Laemmli, Nature 227, 680–685 (1970)).

As a result, only polypeptide (MW c.a.20,000) presumed to be interferon and a small amount of the production of ampicillin-resistant gene are detected. Antiviral activity in the reaction mixture of this in vitro transcription-translation system is measured (according to the measurement method noted later) and about 100,000 u/ml of IFN is detected. The band of MW c.a. 20,000 is extracted from the gel and the IFN activity of the extract solution is measured to be recognized a positive.

(ii) Expression of IFNαS80A2 in *E. coli*

*E. coli* K-12 C600 is transformed with plasmid pTrp-IFNαS80A2 (FIG. 7(c)) prepared above according to the method of Hanahan et al and the colonies growing on a plate containing 40 μg/ml ampicillin are collected at random.

Next, each colony is cultured overnight in LB(Luria-Bertani) medium containing 40 μg/ml ampicillin and 0.005 ml of this culture is inoculated into 5 ml of M9 medium supplemented 0.5% glucose, 0.5% casamino acid and 40 μg/ml ampicillin and incubated at 37° C. for 8 hours, and 5 ml of this culture is centrifuged. The resulting cell pellet, to which is added 2 ml of PBS (phosphate buffered saline) buffer solution supplemented 1% SDS, is destroyed by sonication to provide *E. coli* extract.

In determining a titer of IFN, a value determined by the dye uptake method employing Sindbis virus and FL cell (Protein, Nucleic acid and Enzyme (extra issue) 25, 355–363) is converted into international unit by standardizing the value with NIH human leukocyte IFN standard (G-023-901-527).

The titer of IFN in each *E. coli* extract prepared above is determined to be 10,000–50,000μ per 1 ml of the culture of *E. coli*. This IFN activity is neutralized only by the antibody against human IFNα but not at all by the antibody against human IFNβ or γ.

II

Expression of IFNαS17H9 and αS51B10

The expression is carried out in *E. coli* with the recombinant plasmid having promoter prepared above.

For example, *E. coli* K-12 (C600) is transformed with the recombinant plasmid pTrp-IFNαS17H9 or pTrp-IFNαS51B10 (FIG. 9 (b)) having Trp-promoter according to the method of Hanahan et al (noted above) and 10–20 strains are appropriately picked up from the colonies growing on a plate containing 40 μg/ml ampicillin.

Next, each colony is cultured overnight in LB (Luria-Bertani) medium containing 40 μg/ml ampicillin and 0.005 ml of this culture is transplanted into 5 ml of M9 medium supplemented 0.5% glucose, 0.5% casamino acid and 40 μg/ml ampicillin and incubated at 37° C. for 8 hours. The cell pellet provided by centrifuging 5 ml of this culture, to which is added 2 ml of PBS (phosphate buffered saline)buffer solution supplemented 1% SDS, is destroyed by sonication to provide *E. coli* extract.

In determining a titer of IFN, a value determined by the dye uptake method employing Sindbis virus and FL cell (Protein, Nucleic acid and Enzyme (extra issue) 25, 355–363) is converted into international unit by standardizing the value with NIH human leukocyte IFN standard (G-023-901-527).

The titer of IFN in each *E. coli* extract prepared above is determined and the IFN activity per 1 ml of the culture of *E. coli* is shown in Table 2. The activity to mouse cell (L0) as well as human cell is determined and compared, and it is found that subtype S51B10 has activity to mouse cell but subtype S17H9 has not.

TABLE 2

| subtype | IFN activity (IU/ml) | |
|---|---|---|
| | FL cell | L0 cell (%) |
| S17H9 | 4,800 (100) | <2 (<0.004) |
| S51B10 | 38,000 (100) | 5,000 (13) |

IFNαS51B10 and IFNαS17H9 provided by this invention have antiviral and anti-tumor activity as other subtypes of IFNα and are useful compounds as a medicine for human and animal. The dose largely depends upon the subject and purpose of administration and the purity of administered IFN. However, these IFNαs may be administered to a normal adult man at a dose of about $10^6$–$10^7$ units (international unit) per day.

What is claimed is:

1. Interferon αS17H9.

* * * * *